United States Patent [19]
Williford et al.

[11] Patent Number: 5,458,890
[45] Date of Patent: Oct. 17, 1995

[54] METHODS AND COMPOSITIONS FOR FLAVORING ORALLY-DELIVERED PRODUCTS

[75] Inventors: John H. Williford, Atherton; Martin Katz, Menlo Park; Sergio Nacht, Los Altos; Chung-Heng Cheng, San Jose; Rajesh A. Patel, San Mateo; Brian J. Picard, Palo Alto, all of Calif.

[73] Assignee: Advanced Polymer Systems, Inc., Redwood City, Calif.

[21] Appl. No.: 711,259

[22] Filed: Jun. 4, 1991

Related U.S. Application Data

[63] Continuation of Ser. No. 596,849, Oct. 12, 1990, abandoned, which is a continuation-in-part of Ser. No. 435,100, Nov. 9, 1989, abandoned.

[51] Int. Cl.$^6$ ............................. A23G 3/00; A23G 3/30
[52] U.S. Cl. .................... 426/3; 426/5; 426/96; 426/650; 426/651
[58] Field of Search ............................ 426/3, 4, 5, 6, 426/650, 651, 534, 535, 536, 537, 538, 96; 428/402.27

[56] References Cited

U.S. PATENT DOCUMENTS

| | | |
|---|---|---|
| 2,827,452 | 3/1958 | Schlenk et al. . |
| 3,061,444 | 10/1962 | Rogers et al. . |
| 3,140,184 | 7/1964 | Robbins . |
| 3,962,463 | 6/1976 | Witzel ........................................ 426/5 |
| 4,001,438 | 1/1977 | Marmo et al. . |
| 4,690,825 | 9/1987 | Won . |
| 4,911,934 | 3/1990 | Yang et al. ................................. 426/5 |
| 4,919,941 | 4/1990 | Zibell ......................................... 426/5 |
| 4,931,295 | 6/1990 | Courtright et al. ....................... 426/96 |
| 4,963,369 | 10/1990 | Song et al. ................................. 426/5 |

OTHER PUBLICATIONS

Kirk–Othmer, Encyclopedia of Chemical Technology, 3rd Ed. John Wiley & Sons 1981, New York, vol. 15 pp. 487–488.
Remington's Pharmaceutical Sciences, Gennaro (ed.) Mack Publishing Co. Easton, Pennsylvania, 1985 pp. 1282–1284.

*Primary Examiner*—Anthony J. Weier
*Attorney, Agent, or Firm*—Townsend and Townsend Khourie and Crew

[57] ABSTRACT

Flavored food and pharmaceutical compositions include one or more flavor additives incorporated within polymeric particles, usually within an internal pore network defined by individual polymeric particles. The polymeric particles are, in turn, dispersed within and/or over a surface of an orally-deliverable matrix material, which is usually a solid or semi-solid substrate. In the case of chewable compositions, the flavor additives will be released into the orally-deliverable matrix material as the composition is chewed and held in the mouth, thus prolonging the flavor of the composition. In the case of dried powders and mixes, the flavor will typically be made available as the product is consumed or be released into the matrix material as the composition is further processed. When two flavors are combined with the polymeric particles, the relative amounts of the additives can be selected to provide simultaneous release and exhaustion of the additives.

78 Claims, 2 Drawing Sheets

METHODS AND COMPOSITIONS FOR FLAVORING ORALLY-DELIVERED PRODUCTS

This is a continuation Ser. No. 07/596,849 filed Oct. 12, 1990, now abandoned which is a continuation-in-part of application Ser. No. 07/435,100 filed on Nov. 9, 1989, now abandoned, the disclosure of which is incorporated herein by reference.

BACKGROUND OF THE INVENTION

1. Field of the Invention

The present invention relates generally to flavored compositions and methods for their preparation. More particularly, the invention relates to compositions and methods for preserving and prolonging flavor additives in foods, gums, medicines, and other orally-delivered products.

The flavoring of foods, gums, medicines, and other orally-delivered compositions is a matter of great concern in a variety of situations. In particular, with the advent of processes and manufactured food products, it has become necessary to take measures to preserve or reintroduce flavors during the preparation of such products. The palatability of many food and drug products is dependent on providing acceptable flavor characteristics which are either absent from the product or degraded by the preparation process. The problem is particularly acute with synthetic foods which are produced from basic proteins, starches, carbohydrates, gums, and the like, where it is necessary to introduce flavors which would otherwise be entirely absent. The problem is of equal concern in non-food products, particularly medicines, where the availability of a pleasing flavor can greatly increase patient compliance with a treatment regimen. Thus, the various pills, tablets, lozenges, and the like, can benefit from having a pleasing flavor.

Of particular concern to the present invention are foods and medicines which are intended to be chewed or held in the mouth for extended periods, such as gums, tablets, lozenges, hard candies, and the like. Maintenance of the pleasing flavor in the product as it is held in the mouth over time can be problematic. Prolongation of the flavor can be enhanced by increasing the initial concentration of the flavor additives in the product. Such initially high concentrations, however, can result in a very uneven flavor profile where the flavor intensity is initially very high at first and diminishes rapidly over time. Moreover, such an approach is of little benefit in preserving volatile flavors over time.

An alternate approach has been to microencapsulate flavors, typically by treating the flavor additive compounds to form a hard shell thereon. Such microencapsulation is of some advantage in preserving flavors over time, but still fails to provide a prolonged, even release of flavors over an extended duration. Thus, it would be desirable to provide improved methods and compositions for both preserving and prolonging the release of flavor additives in various food and medicine products.

2. Description of the Background Art

Microencapsulation of flavor additives in candies, foods, and perfumes is described generally in Kirk-Othmer, *Encyclopedia of Chemical Technology*, 3rd Ed., John Wiley & Sons, 1981, New York, Vol. 15, pp. 487–488. The use of flavoring agents in pharmaceutical compositions is described generally in *Remington's Pharmaceutical Sciences*, Gennaro (ed.), Mack Publishing Co., Easton, Pa., 1985, pp. 1282–1284. U.S. Pat. Nos. 2,827,452; 3,061,444; and 3,140,184, describe the use of carbohydrate complexes as vehicles for preserving flavoring agents in food products. U.S. Pat. No. 4,690,825 generally describes methods suitable for preparing polymeric beads useful in the present invention.

SUMMARY OF THE INVENTION

Flavors in food and pharmaceutical compositions are preserved and prolonged by incorporation in polymeric particles dispersed in an orally-deliverable matrix material. The individual particles each define a network of internal pores, and one or more flavor additives are entrapped in said pore networks. In this way, degradation of the flavor additives is inhibited during manufacture and/or storage of the product, and the flavor is released from the particles to the matrix over a prolonged period as the product is consumed or undergoes further preparation. Prolongation of the flavor is of particular benefit for food and pharmaceutical compositions which are chewed or held in the mouth for extended periods, such as gums, tablets, lozenges, and the like. Preservation of the flavor will be particularly beneficial in dry blends and mixes which undergo subsequent preparation processes, particularly processes which involve the addition of moisture which promotes release of the flavor additives from the polymeric particles. In the latter case, the particles will provide effective protection of the flavor additives against degradation during manufacture and storage of the dry blend or mix prior to final preparation.

The orally-deliverable matrix material may be selected from a wide variety of non-toxic, usually edible or consumable, substances of a type generally intended for eating, chewing, and/or being held in the mouth for extended periods of time. Suitable materials may be selected from the group consisting of gums, latex materials, crystallized sugars, amorphous sugars, fondants, nougats, jams, jellies, pastes, powders, dry blends, dehydrated food mixes, baked goods, batters, doughs, tablets, and lozenges.

In an exemplary embodiment, the particulate particles of the present invention are incorporated internally in a gum or latex matrix in order to provide a chewing gum product. The polymeric particles are substantially non-collapsible cross-linked beads, as described in more detail hereinbelow. The beads are preformed and loaded with one or more desired flavor additives and/or sweeteners. After loading, the polymeric beads are combined with the latex matrix of the gum and formed into sticks (or other suitable geometries) by conventional extrusion techniques.

In a preferred embodiment, the flavor-loaded polymeric particles are dispersed on the surface of the orally-deliverable matrix, either in addition to or as an alternative to internal incorporation within the matrix. Surface application of the particles may be achieved by spreading, dusting, spraying, dipping, rolling, or the like, and the resulting layer of particles will usually have a pleasing appearance similar to that of powdered sugar or other conventional food ingredients. Presence of the flavor-loaded polymeric particles on the surface is advantageous in that the sustained flavor release commences substantially immediately, further in that the oxidation-sensitive flavors are protected from direct exposure to air (which is particularly problematic when the flavors are applied to the surface of a food item), and still further in that the particles are not subjected to any processing steps, such as extrusion, baking, or kneading which might express or degrade the flavors within the beads.

Polymeric particles useful in the present invention each define a network of internal pores open to the exterior, which pores contain the flavor additive or additives of interest. The nature of the beads is not critical, with rigid and elastic, spherical and non-spherical, and degradable and non-degradable, and erodible and non-erodible, particles all being suitable. Preferably, the particles are non-degradable in the digestive tract so that they may pass without substantial decomposition. In the exemplary embodiment, the polymeric particles are substantially non-collapsible beads having a cross-linking density of at least about 10%, more usually in the range from about 20% to 80%. The average bead diameter will range from about 5 µm to 50 µm.

Conveniently, polymeric beads useful in the present invention may be formed by suspension polymerization of suitable monomers in an immiscible phase including a porogen. Generally, the monomers and the porogen are first mixed together, and the resulting mixture then suspended in the immiscible phase, usually an aqueous phase. The immiscible phase is then agitated to form droplets of the monomer mixture, and polymerization of the monomer mixture is initiated to form the desired beads. Once the beads are formed, the porogen may be extracted, the beads cleaned to a desired level, and the flavor additives introduced by absorption. In the case of stable, non-volatile flavors, however, it may be possible to utilize the flavor additive as the porogen (or to combine the additive with a suitable porogen) so that the product of suspension polymerization may be used directly without extraction. In either case, the resulting beads are a dry powder which may be incorporated directly into or onto the matrix material.

Use of the porous polymeric particles of the present invention is particularly advantageous for co-entrapment of flavors when it is desired to release the flavors simultaneously over extended periods of time. While the combination of different flavors in a single food product or other orally-deliverable matrix is known, e.g., combinations of sweet, bitter, salty, spicy, sour, etc., frequently one flavor will be exhausted prior to exhaustion of the other(s). Such non-simultaneous exhaustion can often be overcome by co-entrapment of two or more flavors within a single polymeric particle matrix. By properly choosing the bead characteristics, co-release of the flavors can be achieved with both or all flavors being exhausted substantially simultaneously. Moreover, the release will be prolonged over an extended period for all flavor components.

DESCRIPTION OF THE SPECIFIC EMBODIMENTS

Figure 1:
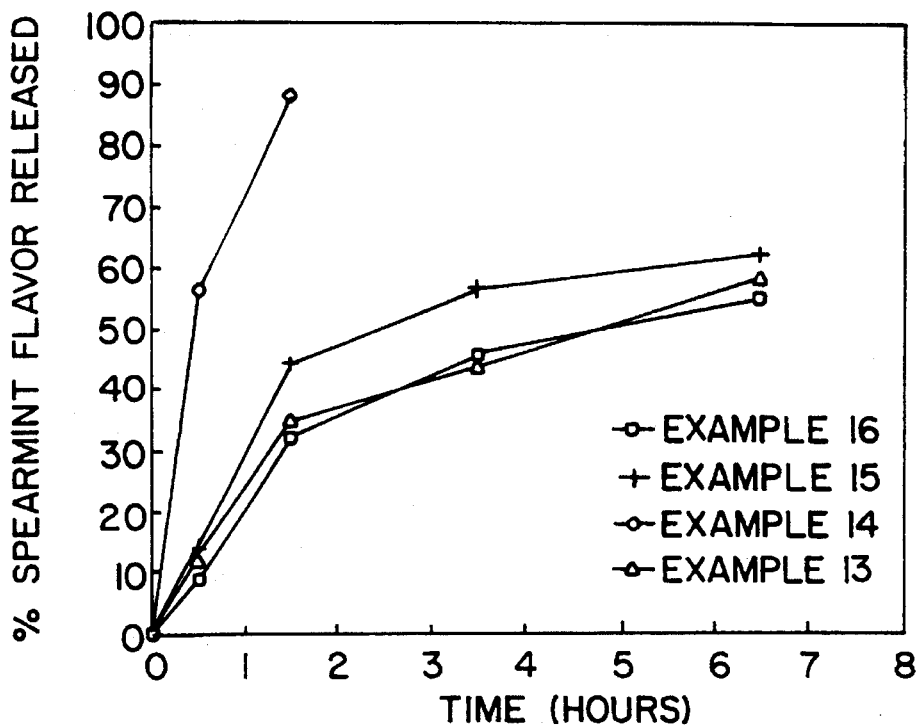
FIG. 1 illustrates the flavor release rate for a spearmint flavor blend from the polymeric particles of the present invention.

According to the present invention, novel food and pharmaceutical compositions comprise an orally-deliverable matrix material having a plurality of polymeric particles dispersed therein and/or thereon. The polymeric particles individually define open pore networks which contain one or more flavor additives. The flavor additives may be released into the matrix material by either of two general mechanisms, depending on the particular type of food or pharmaceutical composition. For compositions which are chewed or held in the mouth for extended periods, the food additives will be gradually released into the matrix and the mouth to prolong the persistence of the flavor sensation. For compositions which are intended to undergo further processing, such as dry blends and mixes, the flavor will be released into the matrix during such subsequent processing steps, such as liquid addition, mixing, and/or heating. In the latter case, degradation of the flavor additives is inhibited and the shelf life of the partially processed food composition is extended.

The methods of the present invention are useful with virtually any type of food or pharmaceutical composition where it is desirable to provide or enhance a flavor. Thus, the present invention will generally find its greatest use with orally-deliverable or consumable food and pharmaceutical compositions, and will be particularly useful with manufactured and processed orally-deliverable products. Such manufactured and processed products will often either lack flavor or require flavor supplementation in order to provide a palatable or pleasing product for the consumer. For example, the natural flavor of many processed foods is lost during processing, and it is necessary to reintroduce or supplement the flavor. Alternatively, synthetic foods and chewing gums will normally lack intrinsic flavoring and require the addition of additives, with the additives of the present invention being particularly suitable.

The food and pharmaceutical compositions of the present invention will generally comprise an orally-deliverable matrix material which will usually be a solid or semi-solid (non-liquid) material formed by conventional food or pharmaceutical processing techniques. The polymeric particles containing the desired food additive(s) may be combined internally within the matrix material at an appropriate point prior to solidification or final processing of the matrix to allow mixing and uniform dispersion of the polymeric particles within the final matrix form. In some cases, however, it may be desirable to have a non-uniform dispersion or surface coating on the matrix, and in such cases it may be possible to apply or impregnate the polymeric particles into the matrix material at a later stage of processing after the matrix material has been solidified or otherwise substantially formed.

Food compositions according to the present invention will include both consumable products as well as non-consumable preparations, such as chewing gums, bubble gums, and the like.

Consumable food compositions include confections, such as candies, jams, jellies, fillings, fondants, nougats, and the like; baked goods, such as cakes, cookies, pies, breads, pastries, and the like; processed dairy products, such as processed cheeses, cottage cheeses, yogurts, and the like, as well as synthetic foods. The class of synthetic foods comprises a variety of food products prepared to mimic various natural food products, particularly meats, shellfish, and the like. Such synthetic foods are generally prepared from basic protein sources, such as single cell protein, soy protein, and the like, and require the addition of flavor additives in order to achieve a desired flavoring. The flavor-impregnated polymeric particles of the present invention is particularly suitable for use in the preparation of such synthetic food products.

The present invention will also find particular use with dried blends and mixes which are used as intermediate formulations for preparing final food products prior to consumption. Such dry blends and mixes include cake mixes, pie mixes, filling mixes, biscuit mixes, and the like where it is desired to introduce a flavor additive which can be preserved over long storage periods. The flavor will be released into the orally-deliverable matrix upon the addition of a liquid and mixing of the composition into a desired batter or dough. The flavor then is retained through subsequent processing, typically baking or cooking on a griddle, and remains in the final food product which is consumed.

The present invention will find further use with dried blends for drinks, e.g., instant coffee and tea, and soups which are intended to be consumed directly after the addition of water. In the latter case, the addition of the liquid may result in extraction of the flavor additives from the polymeric particles so that it is present in the liquid at the time of consumption. Alternatively, the flavor may remain substantially within the particles (i.e., when the flavor is an oil and the liquid is aqueous based) during mixing and be available only as the product is consumed. The polymeric particles of the present invention are particularly suitable for combination in dried mixes and powders as the size can be varied to be consistent with the dried powder, so that the particles will not segregate out during processing and storage.

The food matrix materials of the present invention include a wide variety of conventional food ingredients, such as eggs, egg whites, gelatin, casein, starch, pectin, sugar, syrup, syrups, flour, milk, cereals, water, and the like. In the case of non-consumable food products, such as chewing gum, the matrix material will typically be a non-toxic latex or synthetic rubber. The ingredients may be formed into the desired food compositions by conventional preparation techniques, where the polymeric particles are combined with the matrix at any convenient point in the preparation process. The food products may be cooked or uncooked, molded or unmolded, in the form of a powder, paste, solid, semi-solid, or the like. In the case of chewing gums, the polymeric particles will typically be mixed with the natural or synthetic latex material in a conventional mixer until the particles are uniformly dispersed therein. The chewing gum will then be extruded into conventional chewing gum sticks or other portions.

In addition to internal incorporation of the flavor-loaded polymeric particles as described above, the particles may alternatively and/or additionally be applied over a surface of a formed or shaped matrix, such as a gum stick (already extruded), cake (before or after baking), tablet, lozenge, candy, candy bar, or the like. The particles may be applied by a variety of means, including spreading, dusting, spraying, dipping, rolling, and the like, and optionally the particles may be combined with a liquid or other material which promotes adherence of the particles to the surface. Conveniently, the particles may be combined in other powdered compositions which are applied to the matrix product, e.g., powdered sugar applied to cakes, candies, and the like. Alternatively, the particles may be applied as part of a releasing agent used in forming the matrix, e.g., as part of the release agent in forming gum sticks by extrusion.

Given the spherical nature of the polymer particles, and their particle size, they can very conveniently act as lubricants and also prevent the adherence of semi-soft materials like gums to metals like those used in the machinery necessary to process chewing gums. Currently, other materials like finely powdered sugar, cornstarch and the like are used. However, these materials, while affecting the flavor perception by the consumer, may or may not be consistent with the primary flavor used in the chewing gum or intended to be used in the chewing gum. The polymeric particles of this invention can be conveniently loaded with the same flavor and with artificial sweeteners therefore providing the double advantage of giving to the user the same flavor perception as the total gum while, at the same time, maintaining a low calorie intake for this product source. Additionally, another added advantage is that the inclusion of a flavor release system on the outside of the gum provides faster and greater initial flavor impact which is considered highly desirable in this type of product.

The flavored compositions of the present invention will also include a variety of pharmaceutically-acceptable dosage forms, such as tablets, lozenges, pills, capsules, powders, liquids, suspensions, emulsions, aerosols, or the like, with solid dosage forms being particularly benefitted by the controlled-flavor release characteristics of the present invention. Such dosage forms will include one or more pharmacologically-active substance(s), a pharmaceutically-acceptable excipient, the additive-containing polymeric particles as described above, and, in addition, may contain other medicinal agents, pharmaceutical agents, carriers, adjuvants, etc.

For solid dosage forms, suitable matrix materials include but are not limited to, for example, pharmaceutical grades of mannitol, lactose, starch, magnesium stearate, sodium saccharin, polyalkylene glycol, talcum, cellulose, glucose, sucrose and magnesium carbonate. If desired, the pharmaceutical composition to be administered may also contain minor amounts of non-toxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in the art; for example, see Remington's Pharmaceutical Sciences, Mack Publishing Company, Easton, PA, 16th Edition, 1980. These methods may be modified to introduce the flavor additives at an appropriate stage of the formulation process where the various ingredients are being combined, typically prior to the final solidification step.

Flavoring additives suitable for use in the compositions of the present invention include a wide variety of compounds and substances which can provide a desired flavoring or sweetening sensation in the food or pharmaceutical product. Suitable flavoring additives will be non-toxic and capable of being incorporated within the polymeric particles, as described in more detail hereinbelow. The additives can be solids, semi-solids, liquids, or combinations thereof, and may further be present in a solvent or carrier fluid when introduced to the polymeric particles. The solvent or carrier fluid may then remain in the pores of the particle or may alternatively be evaporated or extracted to leave only the flavoring and/or sweetening component(s).

A compilation of suitable flavoring additives can be found in the United States Code of Federal Regulations (CFR) at 21 CFR Parts 170–197. Further information on suitable flavoring additives may be found in *Furia and Pellanca, Fenaroli's Handbook of Flavor Ingredients*, The Chemical Rubber Co., Cleveland, Ohio, 1971, the disclosure of which is incorporated herein by reference. A list of exemplary flavoring additives (including sweeteners) is found in Table 1 hereinbelow.

TABLE 1

FLAVORING ADDITIVES

| | |
|---|---|
| Acacia syrup | Acesulfame K |
| Amyl acetate | Anethole |
| Anise oil | Aromatic elixir |
| Aspartame | Benzaldehyde |
| Benzaldehyde elixir, compound | Caraway |
| | Caraway oil |
| Cardamom oil | Cardamom seed |
| Cardamom spirit, compound | Cardamom tincture, compound |
| Carvone | Cherry juice |
| Cherry syrup | Cinnamon |
| Cinnamon Aldehyde | Cinnamon oil |
| Cinnamon water | Citric acid |
| Citric acid syrup | Clove oil |
| Cocoa | Cocoa syrup |
| Coriander oil | Dextrose |
| Eriodictyon | Eriodictyon fluidextract |
| Eriodictyon syrup, aromatic | Ethyl acetate |
| | Ethyl Propionate |
| Ethyl vanillin | Fennel oil |
| Fructose | Ginger |
| Ginger fluidextract | Ginger oleoresin |
| Glucose | Glycerin |
| Glycyrrhiza | Glycyrrhiza elixir |
| Glycyrrhiza extract | Glycyrrhiza extract, pure |
| Glycyrrhiza fluidextract | Glycyrrhiza syrup |
| Honey | Iso-Alcoholic elixir |
| Lavender oil | Lemon oil |
| Lemon tincture | Limonene |
| Mannitol | Menthol |
| Methyl salicylate | Nutmeg oil |
| Orange, bitter, elixir | Orange, bitter, oil |
| Orange flower oil | Orange flower water |
| Orange oil | Orange peel, bitter |
| Orange peel, sweet, tincture | Orange spirit, compound |
| Orange syrup | Peppermint |
| Peppermint oil | Peppermint spirit |
| Peppermint water | Phenylethyl alcohol |
| Raspberry juice | Raspberry syrup |
| Rosemary oil | Rose oil |
| Rose water | Rose water, stronger |
| Saccharin | Saccharin calcium |
| Saccharin sodium | Sarsaparilla syrup, compound |
| Sorbitol solution | |
| Spearmint | Spearmint oil |
| Sucrose | Sugar |
| Syrup | Thyme oil |
| Tolu balsam | Tolu balsam syrup |
| Vanilla | Vanilla tincture |
| Vanillin | Wild cherry syrup |

Polymeric particles suitable for use in the present invention will be non-toxic and ingestible by humans and other animals. The particles may be rigid or elastic, spherical or non-spherical, degradable or non-degradable, erodible or non-erodible, and the preparation of suitable rigid beads is described in detail below, while the preparation of suitable elastic particles (hydrogels) is described in numerous references, such as Kirk-Othmer, *Encyclopedia of Chemical Technology*, 3rd Ed., John Wiley & Sons, Vol. 15, pp. 656–675 (1981), and U.S. Pat. Nos. 4,058,491; 4,060,678; and 4,071,508. Most particle preparation processes will result in the formulation of spherical beads, but beads having non-spherical asymmetric, and/or irregular geometries will also find use so long as they meet the necessary physical parameters set forth below.

Suitable polymeric particles will not readily undergo unwanted reactions, will be stable over a wide pH range, and will resist moderate oxidation and reduction. The particles should be stable at higher temperatures and have a relatively long shelf life. Desirable physical parameters for the polymeric particles are described in Table 2.

TABLE 2

| | Broad Range | Preferred Range |
|---|---|---|
| Particle Size | 5–100 μm | 10–50 μm |
| Particle Density (Settled Bulk Density) | 0.1–2.0 g/cc | 0.2–1.0 g/cc |
| Pore Volume | 0.1–2.5 cc/g | 0.3–2.0 cc/g |
| Pore Diameter | 0.001–3 μm | 0.003–1 μm |
| Surface Area | 1–500 m$^2$/g | 20–250 m$^2$/g |

The particles may be formed from a wide variety of polymers, including natural polymers such as carboxylmethylcellulose, cellulose acetate phthalate, ethylcellulose, methylcellulose, arabinogalactan, nitrocellulose, propylhydroxycellulose, and succinylated gelatin; and synthetic polymers such as polyvinyl alcohol, polyethylene, polypropylene, polystyrene, polyacrylamide, polyether, polyester, polyamide, polyurea, ethylene vinyl acetate copolymer, polyvinylidene chloride, polyvinyl chloride, polyacrylate, acetal copolymer, polyurethane, polyvinyl pyrrolidone, poly(p-xylene), polymethylmethacrylate, polyvinyl acetate, and polyhydroxyethyl methacrylate.

The preferred polymer particle matrix of the present invention comprises rigid polymeric beads having a substantially non-collapsible pore structure. That is, the beads will substantially retain their internal pore structure even after the porogen (used in formation of the bead as described hereinafter) has been extracted and the pores are empty. Such beads are mechanically stable compared with non-rigid materials, allowing manufacturing, processing, and handling of the beads under relatively rigorous conditions which might result in the rupture or damage of less stable materials. More importantly, the non-collapsible pores facilitate introduction of the food additive, as described in more detail hereinafter. Usually, although not necessarily, the beads will be non-degradable in the digestive tract so that they may pass through the digestive tract without substantial decomposition.

The rigid polymeric beads of the present invention are formed by polymerization and cross-linking of one or more preselected monomers to form a molecular structure having a substantially non-collapsible network of pores resulting from the presence of the porogen during polymerization. At least one monomer will be polyethylenically unsaturated, and usually the polymer will include a monoethylenically unsaturated co-monomer. The degree of cross-linking may then be controlled by adjusting the ratio of monoethylenically unsaturated monomer to polyethylenically unsaturated monomer, as discussed in more detail hereinbelow. The flavor additive is entrapped within the network of pores, and the resulting particles will act to release the additives over time, as described in more detail hereinbelow.

The rigid polymer beads of the present invention will have greater than 10% cross-linking, usually having in the range from about 15% to 80% cross-linking, more usually having in the range from about 25% to 60% cross-linking, and typically being in the range from about 45% to 55% cross-linking. In the case of gel products, the cross-linking will be substantially less, usually being from about 0.1% to 5%. The calculated or theoretical percentage of cross-linking is defined as the weight of polyethylenically unsaturated monomer (or monomers) divided by the total weight of monomer, including both polyethylenically unsaturated and monoethylenically unsaturated monomers.

The beads of the preferred polymer are conveniently formed by suspension polymerization in a liquid-liquid system. In general, a solution containing monomers, a polymerization initiator or catalyst (if used), and an inert but fully miscible liquid porogen is formed which is immiscible with water. The solution is then suspended in an aqueous solution, which generally contains additives such as food grade surfactants and dispersants to promote the suspension. Non-food grade surfactants and dispersants may be employed but will have to be removed from the beads prior to use. Once the suspension is established with discrete droplets of the desired size, polymerization is effected (typically by activating the reactants by either increased temperature or irradiation). Once polymerization is complete, the resulting rigid beads are recovered from the suspension. The beads at this point are solid porous structures, the polymer having formed around the inert, water-immiscible liquid, thereby forming the pore network. The liquid porogen has accordingly served as a "pore-forming agent" and occupies the pores of the formed beads.

Materials suitable as porogens will be liquid substances which meet the following criteria:

1. They are liquids at the temperature of bead formation.
2. They are either fully miscible with the monomer mixture or capable of being made fully miscible by the addition of a minor amount of non-water-miscible solvent;
3. They are immiscible with water, or at most only slightly soluble;
4. They are inert with respect to the monomers, and stable when in contact with any polymerization catalyst used and when subjected to any conditions needed to induce polymerization (such as temperature and radiation); and
5. They are readily extracted from the pore network of the beads once polymerization is complete.

Suitable porogens include a wide range of substances, notably inert, organic solvents. Some of the most convenient examples are alkanes, cycloalkanes, alcohols, esters, amides, and aromatics. Specific examples of such solvents are alkanes of from 5 to 12 carbon atoms, straight or branched chain cycloalkanes of from 5 to 8 carbon atoms, benzene, $C_5$ to $C_{18}$ alcohols, amyl acetate, amyl propionate, and alkyl-substituted benzenes, such as toluene and the xylenes, and combinations thereof. Mixed porogens having different polarity will frequently find use in providing beads having differing degrees of porosity. Extraction of the porogen(s) may be effected by solvent extraction, evaporation, or similar conventional operations. The porogen extraction step accomplishes the removal of unwanted species from the polymerized structures prior to impregnation with the desired active substance. Such unwanted species include unreacted monomers, residual initiators or catalysts, and surface active agents and/or dispersants remaining on the bead surfaces.

Extraction of the porogen may be effected in a variety of ways, depending on the chemical nature of the porogen and its behavior in combination with that of the other species present. For example, the beads may be recovered from the suspension by filtration, preferably using vacuum apparatus (such as a Buchner funnel). The beads are then washed with an appropriate solvent to remove organic species not bound to the polymer, including surfactants having deposited on the bead surfaces from the aqueous phase, unreacted monomers and residual initiators and catalysts, and the porogen itself. An example of such a solvent is isopropanol, either alone or in aqueous solution. Once washing is complete, the solvent itself is removed by drying, for example in a vacuum.

In certain cases, an alternative method of extraction may be used—i.e., where the porogen, unreacted monomer and water will form an azeotrope. In these cases, steam distillation is an effective way of extracting porogen from the beads. This again may be followed by drying under vacuum.

Whatever cleaning process is employed, the resulting beads should have a contaminant level below about 100 ppm, preferably being below about 10 ppm, and more preferably being below about 5 ppm.

Once the beads are rendered dry and free of the porogen and any unwanted organic materials, flavor additive(s) are introduced to the internal pore networks of the individual beads by absorption, typically in a suitable solvent. Such methods of introducing the flavor additive will be described in more detail hereinbelow.

The polymerization process used in preparing the beads of the polymer delivery system can be modified to control both the porosity and the particle diameter of the beads. Particle diameter is controlled primarily by the degree of agitation, with more rigorous agitation causing smaller droplets and hence smaller polymerized beads. The pore diameter and pore volume, in contrast, are controlled by the cross-linking density porogen content, and nature of the porogen. Porosity is increased by changing the amount of cross-linking monomer used, or by increasing the porogen concentration in the monomer mixture, or both. An increase in porosity increases the surface area of the bead and hence the weight percent of the flavor additive which may be held within the bead. Bead diameter is also affected by the concentration of dispersing agent in the immiscible phase.

The bead diameter should be in the range from about 5 to 100 microns. Beads having an average diameter in the range from about 5 microns to no more than about 70 microns are preferred, with a bead diameter in the range from about 10 microns to about 50 microns being particularly preferred.

The pore dimensions within the beads may vary widely, with optimum dimensions depending on the chemical characteristics of the polymers used as well as the diffusive characteristics of the active substance. Different systems will thus call for different optimum ranges of pore volume distribution to obtain the most desirable properties for the overall formulation. In general, however, best results are obtained with total pore volumes ranging from about 0.1 to about 2.0 cc/g, preferably from about 0.3 to about 1.5 cc/g; pore surface areas ranging from about 1 to about 500 $m^2/g$, preferably from about 20 to about 200 $m^2/g$; and average pore diameters ranging from about 0.001 to about 3.0 microns, preferably from about 0.003 to about 1.0 micron. Following conventional methods of measuring and expressing pore sizes, the pore diameters are measured by techniques such as nitrogen adsorption or mercury porosimetry and are based on the model of a pore of cylindrical shape.

In order to form the cross-linked polymer beads of the present invention, it is necessary to polymerize either polyethylenically unsaturated monomers, i.e., those having at least two sites of unsaturation, or to polymerize monoethylenically unsaturated monomers in the presence of one or more polyethylenically unsaturated monomers. In the latter case, the percentage of cross-linking may be controlled by balancing the relative amounts of monoethylenically unsaturated monomer and polyethylenically unsaturated monomer.

Monoethylenically unsaturated monomers generally suitable for preparing polymer beads for the polymer delivery system include ethylene, propylene, isobutylene, diisobutylene, styrene, ethylvinylbenzene, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters; 2-(dimethylamino) ethyl methacrylate; vinyl esters, including vinyl acetate, vinyl propionate, vinyl butyrate and vinyl laurate; vinyl ketones, including vinyl methyl ketone, vinyl ethyl ketone, vinyl isopropyl ketone, and methyl isopropenyl ketone; vinyl ethers, including vinyl methyl ether, vinyl ethyl ether, vinyl propyl ether, and vinyl isobutyl ether; vinyl pyridine; amides; anhydrides; aldehydes; and the like.

Polyethylenically unsaturated monomers which ordinarily act as though they have only one unsaturated group, such as isopropene, butadiene and chloroprene, may be used as part of the monoethylenically unsaturated monomer content.

Polyethylenically unsaturated cross-linking monomers suitable for preparing such polymer beads include diallyl phthalate, ethylene glycol diacrylate, ethylene glycol dimethacrylate, trimethylolpropanetrimethacrylate, divinylsulfone; polyvinyl and polyallyl ethers of ethylene glycol, of glycerol, of pentaerythritol, of diethyleneglycol, of mono-thio- and dithio-derivatives of glycols, and of resorcinol; divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, divinyl naphthalene, divinylbenzene, trivinylbenzene; alkyldivinylbenzenes having from 1 to 4 alkyl groups of 1 to 2 carbon atoms substituted on the benzene nucleus; alkyltrivinylbenzenes having 1 to 3 alkyl groups of 1 to 2 carbon atoms substituted on the benzene nucleus; trivinylnaphthalenes, and polyvinylanthracenes.

A preferred polymer delivery system of the present invention is formed by the copolymerization of methylmethacrylate and ethylene glycol dimethylmethacrylate. Usually, the methylmethacrylate will be present at from about 10 to 80 percent of the monomer mixture, more usually at about 20 to 60 percent of the monomer mixture, typically being in the range from about 45 to 55 percent of the monomer mixture, with the ethylene glycol dimethylmethacrylate forming the remainder of the mixture.

The particularly preferred polymer delivery system is formed by copolymerization of styrene and divinylbenzene. Usually, the styrene will be present at about 40 to 90 percent of the monomer mixture, more usually being present at about 45 to 80 percent, with divinylbenzene forming the remainder of the mixture.

Depending on its particular nature, the flavoring additives may be introduced to the pore networks of the polymeric particles either in combination with the porogen utilized in the preparation of such particles or by absorption into preformed particles from which the porogen has been extracted. Flavor additives which are stable under the conditions of polymerization and compatible with a desired porogen may be combined with the porogen prior to synthesis, and the resulting product incorporated directly in the orally-deliverable matrix after purification. The porogen may be non-toxic and ingestible and/or extractable, and the resulting porogen-flavor additive combination may be used with or without extraction in the food and pharmaceutical compositions of the present invention.

More commonly, volatile and degradable flavor additives will be introduced to preformed polymeric particles by conventional absorption techniques. Liquid flavor additives may be absorbed either with dilution in an appropriate solvent or without dilution (neat), depending on the viscosity of the flavor additive and the desired release rate from the polymeric particle. Solid flavor additives may be dissolved or dispersed within a suitable solvent, and the solvent then absorbed into the particles by conventional absorption techniques.

In some cases, it will be desirable to introduce at least two flavor additives to the same polymeric particles so that simultaneous release of the flavors can be achieved. By properly selecting the relative amounts of the two (or more) flavor additives which are loaded into the particles, the composition can be programmed to become depleted, i.e., release the entire content of each flavor additive, simultaneously. This is particularly advantageous in chewable compositions where a proper balance of two or more flavors is desired and premature depletion of any one flavor can upset the desired balance.

The loading of two or more flavor additives can also be used to achieve a balance between hydrophobic and hydrophilic flavor agents. The preferred styrene-divinylbenzene and methylmethacrylate-ethylene glycol dimethylmethacrylate beads of the present invention are hydrophobic. The release of hydrophobic flavor additives, such as oils, e.g., mint oil, can be problematic as the flavors will be released more slowly than desired for certain applications. To enhance the release rate, the particles may be preloaded with a desired hydrophilic flavor additive, such as a sweetener. Alternatively, when no second flavor additive is desired the particles may be preloaded with a non-flavored hydrophilic or neutral release agent, such as methyl cellulose, gums, polyvinyl alcohol, poly-ols, or the like. Of course, it will be possible to preload or coat only a portion of the polymeric particles so that some particles will release flavor(s) more slowly than others.

Since these polymeric particles can be programmed to release flavor at various times, appropriate mixtures of polymeric particles loaded with the same or with different flavors can be prepared so that some of them will release flavor very rapidly to provide initial flavor impact, while others with the same or with different flavors can release flavor more slowly, provide for an extended perception of flavor or even a sequential perception of various flavors.

The present invention is particularly suitable for the introduction of flavor additives to chewing gums, where the orally-deliverable matrix material is a natural or synthetic latex, typically being styrene-butadene rubber or chicle. The desired flavor compositions are incorporated into the polymeric beads as described above, and the beads combined with the gum matrix by mixing.

Specific examples of the preparation of gum compositions according to the present invention are set forth in the Experimental section hereinbelow.

The following experiments are offered by way of illustration, not by way of limitation.

EXPERIMENTAL

EXAMPLE 1

1.0 gram of 70% benzoyl peroxide was dissolved in a mixture of 35.2 grams of methyl methacrylate, 52.7 grams of ethylene glycodimethacrylate, and 101.5 grams of toluene. The solution above was mixed with an aqueous solution of 2.7 grams of gum arabic, 2.7 grams of Marasperse® N-22 (sodium-base lignosulfonate from American Can Co.), and 270 grams of deionized water in a vessel provided with a stirring rod, a thermometer, a nitrogen inlet, and a reflux condenser. Suspension polymerization was carried out at about 70° C. at a stirring speed of 1200 rpm with the introduction of nitrogen. Polymerization was finished after about 9 hours, and the product consisted of white beads between 1 and 50 microns in diameter. The beads were washed with water and isopropanol, and then dried at 80°–100° C.

EXAMPLE 2

1.0 gram of 70% benzoyl peroxide was dissolved in a mixture of 17.4 grams of methyl methacrylate, 70.4 grams of ethylene glycodimethacrylate, and 101.5 grams of toluene. The solution was mixed with an aqueous solution of 2.7 grams of gum arabic and 2.7 grams of Marasperse® N-22 (sodium-base lignosulfonate from American Can Co.), and 270 grams of deionized water in a vessel provided with a stirring rod, a thermometer, a nitrogen inlet, and a reflux condenser. The suspension polymerization was carried out at about 70° C. at a stirring speed of 1200 rpm with the introduction of nitrogen. Polymerization was finished after about 9 hours, and the product consisted of white beads between 1 and 60 microns in diameter. The beads were washed with water and isopropanol, and then dried at 80°–100° C.

EXAMPLE 3

0.55 gram of 70% benzoyl peroxide was dissolved in a mixture of 9.9 grams of styrene, 12.0 grams of divinylbenzene (55%), and 20 grams of heptane. The solution was then mixed with an aqueous solution of 0.72 gram of Marasperse® N-22, 0.72 gram of gum arabic, and 72 grams of deionized water in a vessel provided with a stirring rod, a thermometer, a nitrogen inlet, and a reflux condenser. The suspension polymerization was carried out at about 90° C. with stirring at 1200 rpm with the introduction of nitrogen. Polymerization was finished after 16 hours, and the product consisted of white beads between 1 and 60 microns in diameter. The beads were washed with water and isopropanol, and then dried at 80°–100° C.

EXAMPLE 4

0.5 grams of 70% benzoyl peroxide was dissolved in a mixture of 12.3 grams of styrene, 9.6 grams of divinylbenzene (55%), and 27.0 grams of heptane. The solution was then mixed with an aqueous solution of 0.72 grams of Marasperse® N-22 and 0.72 gram of gum arabic, and 72 grams of deionized water in a vessel provided with a stirring rod, a thermometer, a nitrogen inlet, and a reflux condenser. The suspension polymerization was carried out at about 90° C. with stirring at 1200 rpm with the introduction of nitrogen. Polymerization was finished after 16 hours, and the product consisted of white beads between 1 and 60 microns in diameter. The beads are washed with water and isopropanol, and then dried at 80°–100° C.

The surface areas of the purified beads prepared as just described were determined by the B.E.T. method, and the pore volumes were determined by the mercury intrusion method (See Table 3). The B.E.T. method is described in detail in Brunauer, S. Emmet, P. H., and Teller, E., J. Am. Chem. Soc., 60:309–16 (1938). The mercury intrusion method is described in detail in "Advanced Experimental Techniques in Powder Metallurgy", pages 225–252 (Plenum Press, 1970).

TABLE 3

The Porosity Characteristics and Bead Size of Beads

| Example | 1 | 2 | 3 | 4 |
|---|---|---|---|---|
| Pore volume (cc/g) | 0.75 | 0.45 | 1.04 | 1.56 |
| Surface area (m²/g) | 152 | 268 | 158 | 44.5 |
| Bead size (microns, weight average) | 27 | 24 | 26 | 29 |

EXAMPLES 5–16

Entrapments were accomplished by absorbing the active flavor ingredients into the polymer beads. The flavors employed in the following examples were as follows.

A. Mint Flavor Blend

L-Carvone (65%) *

* Weight percent

L-Limonene (20%)

L-Menthol (15%)

| Example | Polymers Used | % Weight Loading of Mint Blend Flavors |
|---|---|---|
| 5 | (Example 1) | 40 |
| 6 | (Example 2) | 40 |
| 7 | (Example 3) | 40 |
| 8 | (Example 4) | 40 |

B, Fruit Flavor Blend

Isoamyl acetate (60%)

Ethyl propionate (30%)

Ethyl acetate (10%)

| Example | Polymers Used | % Weight Loading of Fruit Blend Flavors |
|---|---|---|
| 9 | (Example 1) | 37 |
| 10 | (Example 2) | 38 |
| 11 | (Example 3) | 37 |
| 12 | (Example 4) | 36 |

C. Spearmint

| Example | Polymers Used | % Weight Loading of Spearmint |
|---|---|---|
| 13 | (Example 1) | 40 |
| 14 | (Example 2) | 41 |
| 15 | (Example 3) | 40 |
| 16 | (Example 4) | 40 |

EXAMPLES 17–24

The entrapment of the sweetener was accomplished by mixing the active flavor ingredient and polymer in a water ethanol mixture. A solution of the sweetener in water/ethanol mixture was prepared under conditions of maximum solubility and ingredient stability. The solution was added to the polymer. The solvent was then evaporated. Aspartame and Acesulfame K (SUNETT) were loaded by this process.

TABLE 4

| Example | Type of Polymer | |
|---|---|---|
| | | % Aspartame |
| 17 | Example 1 | 8.0 |
| 18 | Example 2 | 8.0 |
| 19 | Example 3 | 8.6 |
| 20 | Example 4 | 9.3 |
| | | % Acesulfame K |
| 21 | Example 1 | 20 |
| 22 | Example 2 | 20 |
| 23 | Example 3 | 20 |
| 24 | Example 4 | 20 |

EXAMPLE 25

A preliminary feasibility study was conducted to determine if the flavor in a chewing gum could be extended beyond the normal period (10 minutes) by preparing chewing gums containing flavors entrapped in polymeric particles. Sugarless chewing gum base containing 33% beeswax and 77% Vistanex LM-MH (Polyisobutylene) was prepared. Two sets of chewing samples, one containing the Wrigley non-polar mint flavor freely dispersed in the chewing base and the other containing the Wrigley non-polar mint flavor entrapped in styrene-divinylbenzene particles (Example 7) were prepared using this base.

These chewing gum samples were evaluated by a group of four volunteers. Each volunteer evaluated both the chewing gum samples. The general consensus among all the volunteers was that the flavor in the chewing gum containing the flavor entrapped in the polymeric particles lasted longer than in the chewing gum containing the flavor freely dispersed in the chewing gum base.

EXAMPLE 26

50.4996 grams of flavorless gum base was combined with 0.7041 gram of fruit flavor (Example 11) to a final flavor concentration of 0.55%.

The following procedure was used. A 200 cc sigma blade mixer was heated to 110° F. The gum base was preheated in a microwave oven at high setting for 10–30 seconds. The gum base was softened and added to the mixer and allowed to mix for approximately 30 seconds. The flavor was then added to the mixer over a 20–30 second period. The combination was mixed for another 60–90 seconds (not exceeding a total of 2½ minutes mix time). The gum was then removed from the mixer and rolled to stick thickness on waxed paper while warm.

A control was prepared by adding neat flavor to the flavorless gum base per the given procedure. The final concentration of flavor in the gum base was 0.54 w/w %. fruit flavor. Samples of both the control and flavored gum preparations were given to volunteers. These samples were not identified. Each subject was instructed to observe differences. The consensus among the volunteers was that gum containing entrapped flavor tasted "fruity" longer.

EXAMPLE 27

Flavor release rates were determined using a modified USP Dissolution Apparatus, with distilled water as dissolution medium at 32° C. The release rates from the samples of Examples 13–16 of entrapped spearmint were measured over a period of 6.5 hours. The results of this study are shown on FIG. 1.

Figure 2:
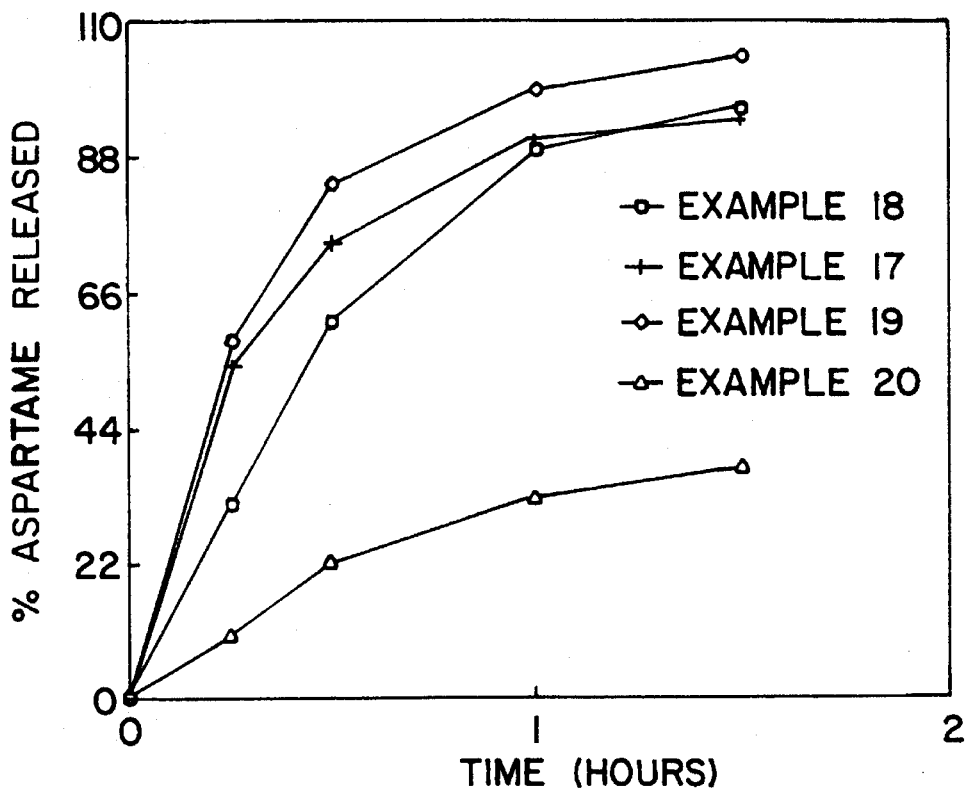
FIG. 2 illustrates the flavor release rate for aspartame sweetener from the polymeric particles of the present invention.

Flavor release rates for aspartame were determined by the same methodology as above. The dissolution medium was water-ethanol mixture at a ratio of 75/25, temperature 22° C. and the release rate was studied over a period of 1.5 hours. The results of this study are shown on FIG. 2.

Figure 3:
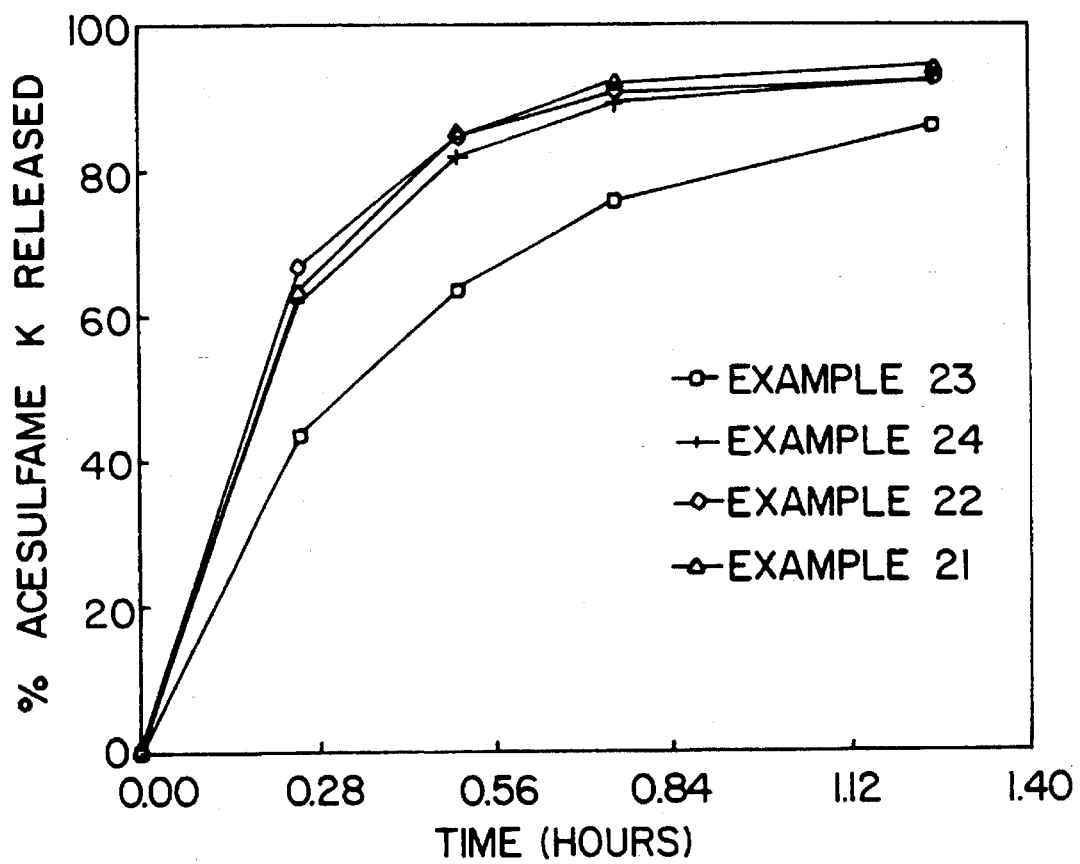
FIG. 3 illustrates the flavor release rate for acesulfame K sweetener from the polymeric particles of the present invention.

A similar release rate determination was also made for acesulfame K using identical equipment and procedures. The results are shown in FIG. 3.

In each of the above cases, an appropriate receptor fluid was selected based on the solubility of the functional ingredient. The data show that each flavor can be released at a controlled rate by use of the appropriate polymer with the right physical characteristics.

EXAMPLE 28

Sticks of gum were prepared by conventional procedures containing Spearmint flavor. These gums were loaded with microspheric particles containing entrapped Spearmint (Examples 13, 16) or Aspartame (Examples 18 to 20).

These same particles were carefully sprinkled onto the surface of the gum at an approximate loading of 20 mg per square centimeter. As a control, other gum sticks were prepared just coated with finely powdered sugar. After "aging" for a week at room temperature, all these gums were tested on a double-blind fashion by appropriate panels composed of either laboratory personnel or other persons. These panels were carefully balanced to include both people who frequently chew gum as well as those who seldom chew gum. All samples were tested on a double-blind fashion and the consumers were questioned as to intensity of impact, both in terms of flavor and sweeteners, and duration. It was found that in those gums prepared with the microspheres loaded with either the flavor or the sweetener coating the gum, a significantly increased perception of flavor and sweeteners was obtained both in terms of the initial time of perception as well as overall intensity, weighted on an arbitrary sensory scale. A trend was also observed, although not statistically significant, for a longer perception of flavor with the microsphere containing gums.

Although the foregoing invention has been described in detail for purposes of clarity of understanding, it will be obvious that certain modifications may be practiced within the scope of the appended claims.

What is claimed is:

1. A flavored composition comprising:

an orally-deliverable matrix material;

a plurality of water insoluable polymeric particles dispersed in said orally-deliverable matrix material, said polymeric particles individually defining networks of internal pores and being non-degradable in the digestive tract; and a flavor additive entrapped within said internal pore networks, whereby the flavor additive is released as the matrix is chewed, dissolved in the mouth, or undergoes further processing selected from the group consisting of liquid addition, dry blending, stirring, mixing, heating, baking, and cooking.

2. A flavored composition as in claim 1, wherein the orally-deliverable matrix material is selected from the group consisting of gums, latex materials, crystallized sugars, amorphous sugars, fondants, nougats, jams, jellies, pastes, powders, dry blends, dehydrated food mixes, baked goods, batters, doughs, tablets, and lozenges.

3. A flavored composition as in claim 1, wherein the flavor additive is selected from the group of additives consisting of

| | |
|---|---|
| Acacia syrup | Acesulfame K |
| Amyl acetate | Anethole |
| Anise oil | Aromatic elixir |
| Aspartame | Benzaldehyde |
| Benzaldehyde elixir, compound | Caraway |
| | Caraway oil |
| Cardamom oil | Cardamom Beed |
| Cardamom spirit, compound | Cardamom tincture, compound |
| Carvone | Cherry juice |
| Cherry syrup | Cinnamon |
| Cinammon Aldehyde | Cinnamon oil |
| Cinnamon water | Citric acid |
| Citric acid syrup | Clove oil |
| Cocoa | Cocoa syrup |
| Coriander oil | Dextrose |
| Eriodictyon | Eriodictyon fluidextract |
| Eriodictyon syrup, aromatic | Ethyl acetate |
| | Ethyl Propionate |
| Ethyl vanillin | Fennel oil |
| Fructose | Ginger |
| Ginger fluidextract | Ginger oleoresin |
| Glucose | Glycerin |
| Glycyrrhiza | Glycyrrhiza elixir |
| Glycyrrhiza extract | Glycyrrhiza extract, pure |
| Glycyrrhiza fluidextract | Glycyrrhiza syrup |
| Honey | Iso-Alcoholic elixir |
| Lavender oil | Lemon oil |
| Lemon tincture | Limonene |
| Mannitol | Menthol |
| Methyl salicylate | Nutmeg oil |
| Orange, bitter, elixir | Orange, bitter, oil |
| Orange flower oil | Orange flower water |
| Orange oil | Orange peel, bitter |
| Orange peel, sweet, tincture | Orange spirit, compound |
| Orange syrup | Peppermint |
| Peppermint oil | Peppermint spirit |
| Peppermint water | Phenylethyl alcohol |
| Raspberry iuice | Raspberry syrup |
| Rosemary oil | Rose oil |
| Rose water | Rose water, stronger |
| Saccharin | Saccharin calcium |
| Saccharin sodium | Sarsaparilla syrup, compound |
| Sorbitol solution | |
| Spearmint | Spearmint oil |
| Sucrose | Sugar |
| Syrup | Thyme oil |
| Tolu balsam | Tolu balsam syrup |
| Vanilla | Vanilla tincture |
| Vanillin | Wild cherry syrup |

4. A composition as in claim 1, wherein said polymeric particles are substantially non-collapsible beads.

5. A composition as in claim 4, wherein said polymeric beads have a cross-linking density of at least about 10%.

6. A composition as in claim 5, wherein said cross-linking density is in the range from about 15% to 80%.

7. A composition as in claim 1, wherein said particles have an average diameter in the range from about 5 μm to 100 μm.

8. A composition as in claim 7, wherein said average diameter is in the range from about 10 μm to 50 μm.

9. A composition as in claim 1, wherein the polymeric particles are a styrene-divinylbenzene copolymer.

10. A composition as in claim 1, wherein the polymeric particles are a methyl methacrylate-ethylene glycol dimethylmethacrylate copolymer.

11. A method for flavoring an edible composition, said method comprising:

dispersing a plurality of water-insoluble polymeric particles within an orally-deliverable matrix material, said polymeric particles and being non-degradable in the digestive tract individually defining open networks of internal pores which entrap a flavor additive therein to form the composition, whereby the flavor additive may be released from the particles as the composition is chewed, dissolved in the mouth, or undergoes further processing selected from the group consisting of liquid addition, dry blending, stirring, mixing, heating, baking, and cooking.

12. A method as in claim 11, wherein the orally-deliverable matrix material is selected from the group consisting of gums, latex materials, crystallized sugars, amorphous sugars, fondants, nougats, jams, jellies, pastes, powders, dry blends, dehydrated food mixes, baked goods, batters, doughs, tablets, and lozenges.

13. A method as in claim 11, wherein the orally-deliverable matrix is a gum or latex material, further comprising extruding the matrix into a chewing gum shape selected from the group consisting of sticks, plugs, tubes, and granules after the polymeric particles have been dispersed therein.

14. A method as in claim 11, wherein the flavor additive is selected from the group of additives consisting of

| | |
|---|---|
| Acacia syrup | Acesulfame K |
| Amyl acetate | Anethole |
| Anise oil | Aromatic elixir |
| Aspartame | Benzaldehyde |
| Benzaldehyde elixir, Compound | Caraway |
| | Caraway oil |
| Cardamom oil | Cardamom seed |
| Cardamom spirit, compound | Cardamom tincture, compound |
| Carvone | Cherry iuice |
| Cherry syrup | Cinnamon |
| Cinammon Aldehyde | Cinnamon oil |
| Cinnamon water | Citric acid |
| Citric acid syrup | Clove oil |
| Cocoa | Cocoa syrup |
| Coriander oil | Dextrose |
| Eriodictyon | Eriodictyon fluidextract |
| Eriodictyon syrup, aromatic | Ethyl acetate |
| | Ethyl Propionate |
| Ethyl vanillin | Fennel oil |
| Fructose | Ginger |
| Ginger fluidextract | Ginger oleoresin |
| Glucose | Glycerin |
| Glycyrrhiza | Glycyrrhiza elixir |
| Glycyrrhiza extract | Glycyrrhiza extract, pure |
| Glycyrrhiza fluidextract | Glycyrrhiza syrup |
| Honey | Iso-Alcoholic elixir |
| Lavender oil | Lemon oil |
| Lemon tincture | Limonene |
| Mannitol | Menthol |
| Methyl salicylate | Nutmeg oil |
| Orange, bitter, elixir | Orange, bitter, oil |
| Orange flower oil | Orange flower water |
| Orange oil | Orange Peel, bitter |
| Orange neel, sweet, tincture | Orange spirit, compound |
| Orange syrup | Peppermint |
| Peppermint oil | Peppermint spirit |
| Peppermint water | Phenylethyl alcohol |
| Raspberry iuice | Raspberry syrup |
| Rosemary oil | Rose oil |
| Rose water | Rose water, strongsr |
| Saccharin | Saccharin calcium |
| Saccharin sodium | Sarsaparilla syrup, compound |
| Sorbitol solution | |
| Spearmint | Spearmint oil |
| Sucrose | Sugar |
| Syrup | Thyme oil |
| Tolu balsam | Tolu balsam syrup |
| Vanilla | Vanilla tincture |
| Vanillin | Wild cherry syrup |

15. A method as in claim 13, wherein the flavor additive is selected from the group consisting of spearmint and fruit.

16. A method as in claim 11, wherein said polymeric particles are substantially non-collapsible beads.

17. A method as in claim 16, wherein said polymeric beads have a cross-linking density of at least about 10%.

18. A method as in claim 17, wherein said cross-linking density is in the range from about 15% to 80%.

19. A method as in claim 11, wherein said particles have an average diameter in the range from about 5 μm to 100 μm.

20. A method as in claim 18, wherein said average diameter is in the range from about 10 μm to 50 μm.

21. A method as in claim 11, wherein the polymeric particles are a styrene-divinylbenzene copolymer.

22. A method as in claim 11, wherein the polymeric particles are a methyl methacrylate-ethylene glycol dimethylmethacrylate copolymer.

23. A flavored chewing gum composition comprising:
   a gum matrix material having flavor additive and sweetener incorporated therein; and
   a plurality of water-insoluable polymeric particles dispersed in said gum matrix material, said polymeric particles individually defining networks of internal pores and being non-degradable in the digestive tract, wherein at least a portion of the flavor additive or sweetener is entrapped within said internal pore networks, whereby the flavor additive or sweetener is released as the gum is chewed.

24. A flavored chewing gum composition as in claim 23, wherein the gum matrix is selected from the group consisting of styrene-butadiene rubber and chicle.

25. A flavored chewing gum composition as in claim 23, wherein both the flavor additive and the sweetener are at least partly entrapped within said internal pore networks, whereby the sweetener is released as the gum is chewed.

26. A flavored chewing gum composition as in claim 23, wherein the flavor additive is selected from the group consisting of spearmint and fruit.

27. A flavored chewing gum composition as in claim 23, wherein said polymeric particles are substantially non-collapsible beads.

28. A flavored chewing gum composition as in claim 23, wherein said polymeric beads have a crosslinking density of at least about 10%.

29. A flavored chewing gum composition as in claim 28, wherein said cross-linking density is in the range from about 15% to 80%.

30. A flavored chewing gum composition as in claim 23, wherein said particles have an average diameter in the range from about 5 μm to 100 μm.

31. A flavored chewing gum composition as in claim 30, wherein said average diameter is in the range from about 10 μm to 50 μm.

32. A flavored chewing gum composition as in claim 23, wherein the polymeric particles are a styrene-divinylbenzene copolymer.

33. A flavored chewing gum composition as in claim 23, wherein the polymeric particles are a methyl methacrylate-ethylene glycol dimethylmethacrylate copolymer.

34. A flavored composition comprising:
   an orally-deliverable matrix material;
   a plurality of water-insoluble polymeric particles dispersed externally over a surface of said orally-deliverable matrix material, said polymeric particles individually defining networks of internal pores; and
   a flavor additive entrapped within said internal pore networks, whereby the flavor additive is released as the matrix is chewed, or dissolved in the mouth.

35. A flavored composition as in claim 34, further comprising an additional quantity of said polymeric particles dispersed internally within said orally-deliverable matrix material.

36. A flavored composition as in claim 34, wherein the orally-deliverable matrix material is selected from the group consisting of gums, latex materials, crystallized sugars, amorphous sugars, fondants, nougats, jams, jellies, pastes, baked goods, tablets, and lozenges.

37. A flavored composition as in claim 34, wherein the flavor additive is selected from the group of additives consisting of

| | |
|---|---|
| Acacia syrup | Acesulfame K |
| Amyl acetate | Anethole |
| Anise oil | Aromatic elixir |
| Aspartame | Benzaldehyde |
| Benzaldehyde elixir, compound | Caraway |
| Cardamom oil | Caraway oil |
| Cardamom spirit, compound | Cardamom seed |
| | Cardamom tincture, compound |
| Carvone | Cherry juice |
| Cherry syrup | Cinnamon |
| Cinammon Aldehyde | Cinnamon oil |
| Cinnamon water | Citric acid |
| Citric acid syrup | Clove oil |
| Cocoa | Cocoa syrup |
| Coriander oil | Dextrose |
| Eriodictyon | Eriodictyon fluidextract |
| Eriodictyon syrup, aromatic | Ethyl acetate |
| | Ethyl Propionate |
| Ethyl vanillin | Fennel oil |
| Fructose | Ginger |
| Ginaer fluidextract | Ginger oleoresin |
| Glucose | Glycerin |
| Glycyrrhiza | Glycyrrhiza elixir |
| Glycyrrhiza extract | Glycyrrhiza extract, pure |
| Glycyrrhiza fluidextract | Glycyrrhiza Byrup |
| Honey | Iso-Alcoholic elixir |
| Lavender oil | Lemon oil |
| Lemon tincture | Limonene |
| Mannitol | Menthol |
| Methyl salicylate | Nutmeg oil |
| Orange, bitter, elixir | Orange, bitter, oil |
| Orange flower oil | Orange flower water |
| Orange oil | Orange peel, bitter |
| Orange peel, sweet, tincture | Orange spirit, compound |
| Orange syrup | Peppermint |
| Peppermint oil | Peppermint spirit |
| Peppermint water | Phenylethyl alcohol |
| Raspberry juice | Raspberry syrup |
| Rosemary oil | Rose oil |
| Rose water | Rose water, stronger |
| Saccharin | Saccharin calcium |
| Saccharin sodium | Sarsaparilla syrup, compound |
| Sorbitol solution | |
| Spearmint | Spearmint oil |
| Sucrose | Sugar |
| Syrup | Thyme oil |
| Tolu balsam | Tolu balsam syrup |
| Vanilla | Vanilla tincture |
| Vanillin | Wild cherry syrup |

38. A composition as in claim 34, wherein said polymeric particles are substantially non-collapsible copolymer beads having a cross-linking density of at least about 10% and an average diameter in the range from about 5 μm to 100 μm.

39. A composition as in claim 38, wherein the polymeric particles are a styrene-divinylbenzene copolymer.

40. A composition as in claim 38, wherein the polymeric particles are a methyl methacrylate-ethylene glycol dimethylmethacrylate copolymer.

41. A method for flavoring an edible composition, said method comprising:
   applying a plurality of water-insoluble polymeric particles over the surface of an orally-deliverable matrix material after forming of said matrix material, said polymeric particles and being non-degradable in the digestive tract individually defining open networks of internal pores which entrap a flavor additive therein to form the composition, whereby the flavor additive may be released from the particles as the composition is chewed, dissolved in the mouth.

42. A method as in claim 41, wherein the polymeric particles are applied by spreading, dusting, spraying, dipping, coating, or rolling.

43. A method as in claim 41, further comprising dispersing an additional quantity of said polymeric particles within the orally-deliverable matrix material prior to forming.

44. A method as in claim 41, wherein the orally-deliverable matrix material is selected from the group consisting of gums, latex materials, crystallized sugars, amorphous sugars, fondants, nougats, jams, jellies, pastes, powders, baked goods, tablets, and lozenges.

45. A method as in claim 41, wherein the orally-deliverable matrix is a gum or latex material which has been extruded prior to applying the polymeric particles thereon.

46. A method as in claim 41, wherein the flavor additive is selected from the group of additves consisting of

| | |
|---|---|
| Acacia syrup | Acesulfame K |
| Amyl acetate | Anethole |
| Anise oil | Aromatic elixir |
| Aspartame | Benzaldehyde |
| Benzaldehyde elixir, compound | Caraway |
| | Caraway oil |
| Cardamom oil | Cardamom seed |
| Cardamom spirit, compound | Cardamom tincture, compound |
| Carvone | Cherry juice |
| Cherry syrup | Cinnamon |
| Cinammon Aldehyde | Cinnamon oil |
| Cinnamon water | Citric acid |
| Citric acid syrup | Clove oil |
| Cocoa | Cocoa syrup |
| Coriander oil | Dextrose |
| Eriodictyon | Eriodictyon fluidextract |
| Eriodictyon syrup, aromatic | Ethyl acetate |
| | Ethyl Propionate |
| Ethyl vanillin | Fennel oil |
| Fructose | Ginger |
| Ginger fluidextract | Ginger oleoresin |
| Glucose | Glycerin |
| Glycyrrhiza | Glycyrrhiza elixir |
| Glycyrrhiza extract | Glycyrrhiza extract, pure |
| Glycyrrhiza fluidextract | Glycyrrhiza syrup |
| Honey | Iso-Alcoholic elixir |
| Lavender oil | Lemon oil |
| Lemon tincture | Limonene |
| Mannitol | Menthol |
| Methyl | Nutmeg oil |
| Orange, bitter, elixir | Orange, bitter, oil |
| Orange flower oil | Orange flower water |
| Orange oil | Orange peel, bitter |
| Orange peel, sweet, tincture | Orange spirit, compound |
| Orange syrup | Peppermint |
| Peppermint oil | Peppermint spirit |
| Peppermint water | Phenylethyl alcohol |
| Raspberry juice | Raspberry syrup |
| Rosemary oil | Rose oil |
| Rose water | Rose water, stronger |
| Saccharin | Saccharin calcium |
| Saccharin sodium | Sarsaparilla syrup, compound |
| Sorbitol solution | |
| Spearmint | Spearmint oil |
| Sucrose | Sugar |
| Syrup | Thyme oil |
| Tolu balsam | Tolu balsam syrup |

-continued

| | |
|---|---|
| Vanilla | Vanilla tincture |
| Vanillin | Wild cherry syrup |

47. A method as in claim 45, wherein the internal bore networks entrap at least two distinct flavor additives therein.

48. A method as in claim 38, wherein said polymeric particles are substantially non-collapsible beads having a cross-linking density of at least about 10% and an average diameter in the range from about 5 μm to 100 μm.

49. A method as in claim 48, wherein the polymeric particles are a styrene-divinylbenzene copolymer.

50. A method as in claim 48, wherein the polymeric particles are a methyl methacrylate-ethylene glycol dimethylmethacrylate copolymer.

51. A flavored chewing gum composition comprising:
a gum matrix material having flavor additive and sweetener; and
a plurality of water-insoluble polymeric particles dispersed in said gum matrix material, said polymeric particles individually defining networks of internal pores and being non-degradable in the digestive tract, wherein at least a portion of the flavor additive or sweetener is entrapped within said internal pore networks and at least a portion of said polymeric particles are present on the surface of the gum material, whereby the flavor additive or sweetener is released as the gum is chewed.

52. A flavored chewing gum composition as in claim 51, wherein the gum matrix is selected from the group consisting of styrene-butadiene rubber and chicle.

53. A flavored chewing gum composition as in claim 51, wherein both the flavor additive and the sweetener are at least partly entrapped within said internal pore networks, whereby the sweetener is released as the gum is chewed.

54. A flavored chewing gum composition as in claim 51, wherein the flavor additive is selected from the group consisting of spearmint and fruit.

55. A flavored chewing gum composition as in claim 38, wherein said polymeric particles are substantially non-collapsible beads having a cross-linking density of at least about 10% and an average diameter in the range from about 5 μm to 100 μm.

56. A flavored chewing gum composition as in claim 55, wherein the polymeric particles are a styrene-divinylbenzene copolymer.

57. A flavored chewing gum composition as in claim 55, wherein the polymeric particles are a methyl methacrylate-ethylene glycol dimethylmethacrylate copolymer.

58. A flavored composition comprising:
an orally-deliverable matrix material;
a plurality of water-insoluble polymeric particles combined with said orally-deliverable matrix material, said polymeric particles individually defining networks of internal pores and being non-degradable in the digestive tract; and
at least two flavor additives entrapped within said internal pore networks, whereby the flavor additives are released substantially simultaneously as the matrix is chewed, dissolved in the mouth.

59. A flavored composition as in claim 58, wherein said polymeric particles are dispersed internally within the orally-deliverable matrix material.

60. A flavored composition as in claim 58, wherein said polymeric particles are dispersed externally over a surface of the orally-deliverable matrix material.

61. A flavored composition as in claim 58, wherein said polymeric particles are disposed both internally and externally over a surface of the orally-deliverable matrix material.

62. A flavored composition as in claim 58, wherein the at least two flavor additives are present in relative amounts selected so that the flavors become exhausted after the same time period of chewing or dissolving in the mouth.

63. A flavored composition as in claim 58 wherein the orally-deliverable matrix material is selected from the group consisting of gums, latex materials, crystallized sugars, amorphous sugars, fondants, nougats, jams, jellies, pastes, powders, dry blends, dehydrated food mixes, baked goods, batters, doughs, tablets, and lozenges.

64. A flavored composition as in claim 58 wherein each flavor additive is selected from the group of additives consisting of

| | |
|---|---|
| Acacia syrup | Acesulfame K |
| Amyl acetate | Anethole |
| Anise oil | Aromatic elixir |
| Aspartame | Benzaldehyde |
| Benzaldehyde elixir, compound | Caraway |
| | Caraway oil |
| Cardamom oil | Cardamom seed |
| Cardamom spirit, compound | Cardamom tincture, compound |
| Carvone | Cherry juice |
| Cherry syrup | Cinnamon |
| Cinammon Aldehyde | Cinnamon oil |
| Cinnamon water | Citric acid |
| Citric acid syrup | Clove oil |
| Cocoa | Cocoa syrup |
| Coriander oil | Dextrose |
| Eriodictyon | Eriodictyon fluidextract |
| Eriodictyon syrup, aromatic | Ethyl acetate |
| | Ethyl Propionate |
| Ethyl vanillin | Fennel oil |
| Fructose | Ginger |
| Ginger fluidextract | Ginger oleoresin |
| Glucose | Glycerin |
| Glycyrrhiza | Glycyrrhiza elixir |
| Glycyrrhiza extract | Glycyrrhiza extract, pure |
| Glycyrrhiza fluidextract | Glycyrrhiza syrup |
| Honey | Iso-Alcoholic elixir |
| Lavender oil | Lemon oil |
| Lemon tincture | Limonene |
| Mannitol | Menthol |
| Methyl salicylate | Nutmeg oil |
| Orange, bitter, elixir | Orange, bitter, oil |
| Peppermint oil | Peppermint spirit |
| Peppermint water | Phenylethyl alcohol |
| Raspberry juice | Raspberry syrup |
| Rosemary oil | Rose oil |
| Rose water | Rose water, stronger |
| Saccharin | Saccharin calcium |
| Saccharin sodium | Sarsaparilla syrup, compound |
| Sorbital solution | |
| Spearmint | Spearmint oil |
| Sucrose | Sugar |
| Syrup | Thyme oil |
| Tolu balsam | Tolu balsam syrup |
| Vanilla | Vanilla tincture |
| Vanillin | Wild cherry syrup |

65. A composition as in claim 38, wherein said polymeric particles are substantially non-collapsible beads.

66. A composition as in claim 65, wherein the polymeric particles are a styrene-divinylbenzene copolymer.

67. A composition as in claim 65, wherein the polymeric particles are a methyl methacrylate-ethylene glycol dimethylmethacrylate copolymer.

68. A flavoring composition comprising a plurality of water-insoluble polymeric particles individually defining networks of internal pores and at least two flavor additives entrapped within said internal pore networks.

69. A flavoring composition as in claim 68, wherein at least two flavor additives are present in selective amounts selected so that the flavors will be released simultaneously and become exhausted at substantially the same time.

70. A flavoring composition as in claim 68, wherein each flavor additive is selected from the group of additives consisting of

| | |
|---|---|
| Acacia syrup | Acesulfame K |
| Amyl acetate | Anethole |
| Anise oil | Aromatic elixir |
| Aspartame | Benzaldehyde |
| Benzaldehyde elixir, compound | Caraway |
| | Caraway oil |
| Cardamom oil | Cardamom seed |
| Cardamom spirit, compound | Cardamom tincture, compound |
| Carvone | Cherry juice |
| Cherry syrup | Cinnamon |
| Cinammon Aldehyde | Cinnamon oil |
| Cinnamon water | Citric acid |
| Citric acid syrup | Clove oil |
| Cocoa | Cocoa syrup |
| Coriander oil | Dextrose |
| Eriodictyon | Eriodictyon fluidextract |
| Eriodictyon syrup, aromatic | Ethyl acetate |
| | Ethyl Propionate |
| Ethyl vanillin | Fennel oil |
| Fructose | Ginger |
| Ginger fluidextract | Ginger oleoresin |
| Glucose | Glycerin |
| Glycyrrhiza | Glycyrrhiza elixir |
| Glycyrrhiza extract | Glycyrrhiza extract, pure |
| Glycyrrhiza fluidextract | Glycyrrhiza syruip |
| Honey | Iso-Alcoholic elixir |
| Lavender oil | Lemon oil |
| Lemon tincture | Limonene |
| Mannitol | Menthol |
| Methyl salicylate | Nutmeg oil |
| Orange, bitter, elixir | Orange, bitter, oil |
| Orange flower oil | Orange flower water |
| Orange oil | Orange peel, bitter |
| Orange peel, sweet, tincture | Orange spirit, compound |
| Orange syrup | Peppermint |
| Peppermint oil | Peppermint spirit |
| Peppermint water | Phenylethyl alcohol |
| Raspberry juice | Raspberry syrup |
| Rosemary oil | Rose oil |
| Rose water | Rose water, stronger |
| Saccharin | Saccharin calcium |
| Saccharin sodium | Sarsaparilla syrup, compound |
| Sorbitol solution | |
| Spearmint | Spearmint oil |
| Sucrose | Sugar |
| Syrup | Thyme oil |
| Tolu balsam | Tolu balsam syrup |
| Vanilla | Vanilla tincture |
| Vanillin | Wild cherry syrup |

71. A flavoring composition as in claim 68, wherein said polymeric particles are substantially non-collapsible beads.

72. A flavoring composition as in claim 71, wherein the polymeric particles are a styrene-divinylbenzene copolymer.

73. A flavoring composition as in claim 71, wherein the polymeric particles are a methyl methacrylate-ethylene glycol dimethylmethacrylate copolymer.

74. A flavoring composition as in claim 68, wherein the polymeric particles are hydrophobic and wherein a first hydrophilic flavoring is loaded into the particle followed by a hydrophobic flavor.

75. A chewing gum, comprising:
   a chewing gum base having dispersed therein water-insoluble porous polymeric beads having microporous passages impregnated with a flavoring agent.

76. The chewing gum of claim 75 wherein said polymeric beads comprise a copolymer of styrene and divinylbenzene.

77. A method of making chewing gum with a controlled release flavoring agent comprising the steps of:
 providing a chewing gum base;
 dispersing within the chewing gum base a plurality of water-insoluble porous polymeric beads having microporous passages impregnated with a flavoring agent.

78. The method of claim 77 wherein said polymeric beads comprise a copolymer of styrene and divinylbenzene.

* * * * *